(12) United States Patent
Ourada et al.

(10) Patent No.: US 9,271,783 B2
(45) Date of Patent: Mar. 1, 2016

(54) END-EFFECTOR ASSEMBLY INCLUDING A PRESSURE-SENSITIVE LAYER DISPOSED ON AN ELECTRODE

(71) Applicant: COVIDIEN LP, Mansfield, MA (US)

(72) Inventors: Paul E. Ourada, Longmont, CO (US); Robert H. Wham, Boulder, CO (US)

(73) Assignee: Covidien LP, Mansfield, MA (US)

( * ) Notice: Subject to any disclaimer, the term of this patent is extended or adjusted under 35 U.S.C. 154(b) by 183 days.

(21) Appl. No.: 13/926,491

(22) Filed: Jun. 25, 2013

(65) Prior Publication Data

US 2014/0025074 A1  Jan. 23, 2014

Related U.S. Application Data

(60) Provisional application No. 61/672,344, filed on Jul. 17, 2012.

(51) Int. Cl.
| | | |
|---|---|---|
| *A61B 18/12* | (2006.01) | |
| *A61B 18/14* | (2006.01) | |
| *A61B 18/00* | (2006.01) | |

(52) U.S. Cl.
CPC ......... *A61B 18/1445* (2013.01); *A61B 18/1442* (2013.01); *A61B 2018/00107* (2013.01); *A61B 2018/147* (2013.01)

(58) Field of Classification Search
CPC ............... A61B 2018/1465; A61B 18/1445
USPC ............................................. 606/51, 52, 207
See application file for complete search history.

(56) References Cited

U.S. PATENT DOCUMENTS

| | | | |
|---|---|---|---|
| 3,746,002 | A | 7/1973 | Haller |
| 3,801,766 | A | 4/1974 | Morrison, Jr. |
| 4,126,136 | A | 11/1978 | Auth et al. |
| 5,452,837 | A | 9/1995 | Williamson, IV et al. |
| 5,496,312 | A | 3/1996 | Klicek |
| 5,720,742 | A | 2/1998 | Zacharias |
| 5,810,811 | A | 9/1998 | Yates et al. |
| 5,911,719 | A | 6/1999 | Eggers |
| 5,938,589 | A | 8/1999 | Wako et al. |
| 6,086,586 | A | 7/2000 | Hooven |
| 6,325,795 | B1 | 12/2001 | Lindemann et al. |
| 6,402,747 | B1 | 6/2002 | Lindemann et al. |
| 6,735,470 | B2 | 5/2004 | Henley et al. |
| 6,770,072 | B1 | 8/2004 | Truckai et al. |

(Continued)

FOREIGN PATENT DOCUMENTS

| | | |
|---|---|---|
| EP | 1707151 A2 | 10/2006 |
| WO | 2004/073490 A2 | 9/2004 |

OTHER PUBLICATIONS

Extended European Search Report dated Oct. 29, 2013 for EP 13 17 6633.

*Primary Examiner* — Joseph Stoklosa
*Assistant Examiner* — Jocelyn D Ram

(57) ABSTRACT

An end-effector assembly includes first and second jaw members disposed in opposing relation relative to one another, at least one of the jaw members moveable from an open position to a closed position for grasping tissue therebetween. First and second conductive plates are disposed on opposing surfaces of corresponding first and second jaw members. First and second compressible membranes are configured to electrically connect corresponding first and second conductive plates to a surgical field when subjected to a compression bias.

12 Claims, 9 Drawing Sheets

(56) References Cited

U.S. PATENT DOCUMENTS

| | | |
|---|---|---|
| 6,926,716 B2 | 8/2005 | Baker et al. |
| 6,932,816 B2 | 8/2005 | Phan |
| 7,070,597 B2 | 7/2006 | Truckai et al. |
| 7,125,409 B2 | 10/2006 | Truckai et al. |
| 7,244,257 B2 | 7/2007 | Podhajsky et al. |
| 7,354,440 B2 | 4/2008 | Truckai et al. |
| 7,442,193 B2 * | 10/2008 | Shields et al. ............. 606/49 |
| 7,451,904 B2 | 11/2008 | Shelton, IV |
| 7,594,913 B2 | 9/2009 | Ormsby et al. |
| 7,632,269 B2 | 12/2009 | Truckai et al. |
| 7,789,878 B2 | 9/2010 | Dumbauld et al. |
| 7,803,156 B2 | 9/2010 | Eder et al. |
| 7,955,326 B2 | 6/2011 | Paul et al. |
| 7,955,331 B2 | 6/2011 | Truckai et al. |
| 8,075,558 B2 | 12/2011 | Truckai et al. |
| 8,215,182 B2 | 7/2012 | Artale et al. |
| 8,292,156 B2 | 10/2012 | Kostrzewski |
| 8,474,677 B2 | 7/2013 | Woodard, Jr. et al. |
| 2003/0144652 A1* | 7/2003 | Baker et al. ............... 606/28 |
| 2003/0216732 A1 | 11/2003 | Truckai et al. |
| 2003/0229344 A1 | 12/2003 | Dycus et al. |
| 2004/0116979 A1* | 6/2004 | Truckai ............ A61B 18/1445 607/51 |
| 2004/0143263 A1* | 7/2004 | Schechter et al. ........... 606/51 |
| 2006/0069388 A1* | 3/2006 | Truckai et al. ............. 606/45 |
| 2006/0293656 A1* | 12/2006 | Shadduck et al. .......... 606/51 |
| 2007/0062017 A1 | 3/2007 | Dycus et al. |
| 2007/0213711 A1* | 9/2007 | Eder et al. ................. 606/51 |
| 2007/0233019 A1 | 10/2007 | Forsell |
| 2008/0077200 A1 | 3/2008 | Bendett et al. |
| 2008/0249523 A1 | 10/2008 | McPherson et al. |
| 2008/0281311 A1 | 11/2008 | Dunning et al. |
| 2008/0319292 A1 | 12/2008 | Say et al. |
| 2008/0319434 A1 | 12/2008 | Rick et al. |
| 2009/0206126 A1 | 8/2009 | Huitema et al. |
| 2009/0318914 A1 | 12/2009 | Utley et al. |
| 2010/0179545 A1 | 7/2010 | Twomey et al. |
| 2010/0198220 A1 | 8/2010 | Boudreaux et al. |
| 2011/0036183 A1 | 2/2011 | Artale et al. |
| 2011/0077648 A1 | 3/2011 | Lee et al. |
| 2011/0276045 A1 | 11/2011 | Truckai et al. |
| 2011/0306965 A1* | 12/2011 | Norvell et al. ............. 606/41 |
| 2012/0080499 A1 | 4/2012 | Schall et al. |
| 2012/0116379 A1* | 5/2012 | Yates ............... A61B 17/00234 606/33 |
| 2012/0330308 A1 | 12/2012 | Joseph |
| 2012/0330309 A1 | 12/2012 | Joseph |
| 2013/0178852 A1 | 7/2013 | Allen, IV et al. |
| 2013/0190760 A1* | 7/2013 | Allen, IV .......... A61B 18/1442 606/52 |
| 2015/0066000 A1* | 3/2015 | An ................... A61B 5/1455 606/1 |
| 2015/0190160 A1* | 7/2015 | Kappel ............... A61B 17/29 606/207 |
| 2015/0209102 A1* | 7/2015 | Wyatt ............... A61B 18/1445 606/51 |
| 2015/0223867 A1* | 8/2015 | Brandt ............... A61B 18/1442 606/34 |
| 2015/0223868 A1* | 8/2015 | Brandt ............... A61B 18/1206 606/40 |
| 2015/0230857 A1* | 8/2015 | Horner ............... A61B 18/1445 606/51 |

* cited by examiner

END-EFFECTOR ASSEMBLY INCLUDING A PRESSURE-SENSITIVE LAYER DISPOSED ON AN ELECTRODE

CROSS REFERENCE TO RELATED APPLICATION

The present application claims the benefit of and priority to U.S. Provisional Application Ser. No. 61/672,344, filed on Jul. 17, 2012, the entire contents of which are incorporated herein by reference.

BACKGROUND

The present disclosure relates to a surgery. More particularly, the present disclosure relates to an electrosurgical forceps that includes self-aligning jaws.

TECHNICAL FIELD

Electrosurgical forceps utilize both mechanical clamping action and electrical energy to affect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, in addition to the occurrence of fluid in the surgical field, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

In accordance with the present disclosure, an end-effector assembly of a surgical forceps is provided. An end-effector assembly includes first and second jaw members disposed in opposing relation relative to one another, at least one of the jaw members being moveable from an open position to a closed position for grasping tissue therebetween. First and second conductive plates are disposed on opposing surfaces of corresponding first and second jaw members. First and second compressible membranes are configured to electrically connect corresponding first and second conductive plates to a surgical field when subjected to a compression bias.

The first and second compressible membranes electrically connect corresponding first and second conductive plates through the portions of the first and second compressible membranes adjacent the applied compression bias.

In one aspect, the electrical connection formed between the first and second conductive plates through the corresponding first and second compressible membranes is a capacitive connection. The capacitance of the compressible membranes is configured to vary in magnitude in response to the applied compression bias.

In another aspect, the electrical connection formed between the first and second conductive plates through the first and second compressible membranes is a resistive connection. The resistance of the resistive connection through each of the compressible membranes is responsive to the applied compression bias.

In another aspect, the first and second compressible membranes each include a plurality of switching mechanisms formed on opposing surfaces thereof, each of the plurality of switching mechanisms being responsive to an applied compression bias. Each of the plurality of switching mechanisms forms a low-resistance connection in response to the applied compression bias.

In yet another aspect, the first and second compressible membranes each include one or more pairs of electrically conductive parallel plates, wherein in an uncompressed condition the parallel plates are separated by a non-conductive fluid and form a high-resistance pathway through the compressible membranes and in a compressed condition the parallel plates connect and form a low-resistance pathway though the compressible membranes. At least one of the one or more pairs of electrically conductive parallel plates connects to the conductive plate of one of the jaw members and the corresponding electrically conductive parallel plate connects to an outer surface of a respective compressible membrane of the jaw member. The non-conductive fluid viscosity may be related to the temperature of the compressible membrane. The non-conductive fluid viscosity may be indirectly proportional to the temperature of the compressible membrane.

In yet another aspect, one or both of the first and second compressible membranes includes a compressible material embedded with a plurality of conductive particles. The distance between the conductive particles may be responsive to an applied compression bias and/or the resistance of the compressible material may be responsive to the distance between conductive particles. Alternatively, the capacitance of the compressible material may be responsive to the distance between conductive particles.

BRIEF DESCRIPTION OF THE DRAWINGS

Various embodiments of the subject instrument are described herein with reference to the drawings wherein.

DETAILED DESCRIPTION

Figure 1:
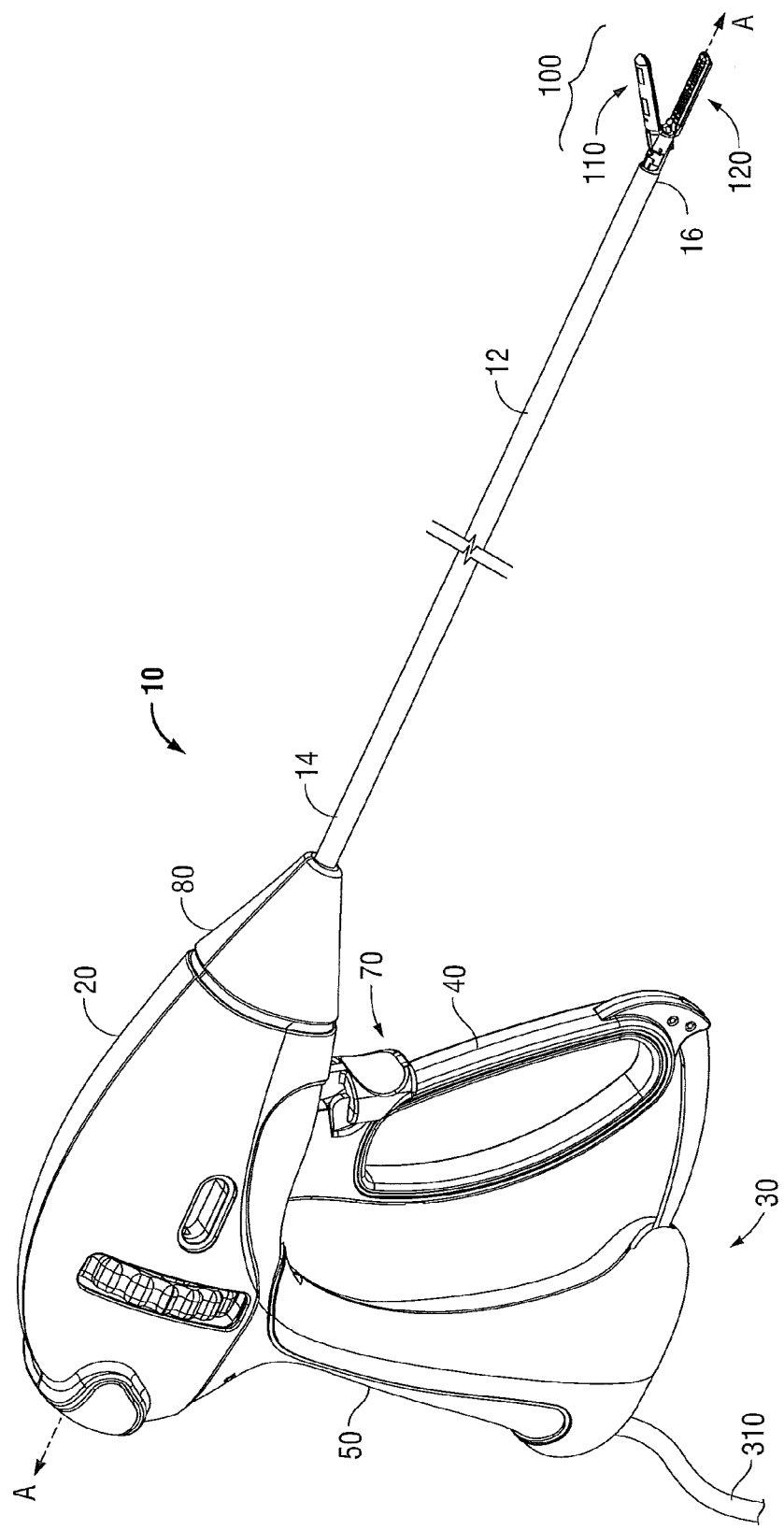
FIG. 1 is a top, perspective view of an alternate embodiment of an endoscopic forceps, including a housing, a handle assembly, a shaft and an end-effector assembly.

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to employ the present disclosure in virtually any appropriately detailed structure. In the drawings and in the descriptions which follow, the term "proximal", as is traditional, will refer to the end of the forceps 10 which is closer to the user, while the term "distal" will refer to the end which is further from the user.

In the present disclosure, conventional electrosurgical conducting surfaces are covered with a compressible membrane. The compressible membrane prevents and/or minimizes leakage current by eliminating direct contact between the electrosurgical conductive surfaces and the surgical field. Application of a compression bias to the compressible membrane alters a mechanical property and/or an electrical property of the compressible membrane thereby forming an electrical connection between the electrosurgical conductive surfaces and the surgical field through the compressible membrane.

Turning now to FIG. 1, an alternate embodiment of an endoscopic forceps 10 is shown that includes a housing 20, a handle assembly 30, a rotating assembly 80, a trigger assembly 70 and an end-effector assembly 100. Forceps 10 further includes a shaft 12 having a distal end 16 configured to mechanically engage end-effector assembly 100 and a proximal end 14 that mechanically engages housing 20. Forceps 10 also includes electrosurgical cable 310 that connects forceps 10 to a generator (not explicitly shown). Cable 310 has sufficient length to extend through shaft 12 in order to provide electrical energy to at least one of the jaw members 110 and 120 of end-effector assembly 100.

Handle assembly 30 includes fixed handle 50 and a moveable handle 40. Fixed handle 50 is integrally associated with housing 20 and handle 40 is moveable relative to fixed handle 50. Rotating assembly 80 is integrally associated with housing 20 and is rotatable approximately 180 degrees in either direction about a longitudinal axis "A" defined through shaft 12. The housing 20 includes two halves that house the internal working components of the forceps 10.

Figure 2:
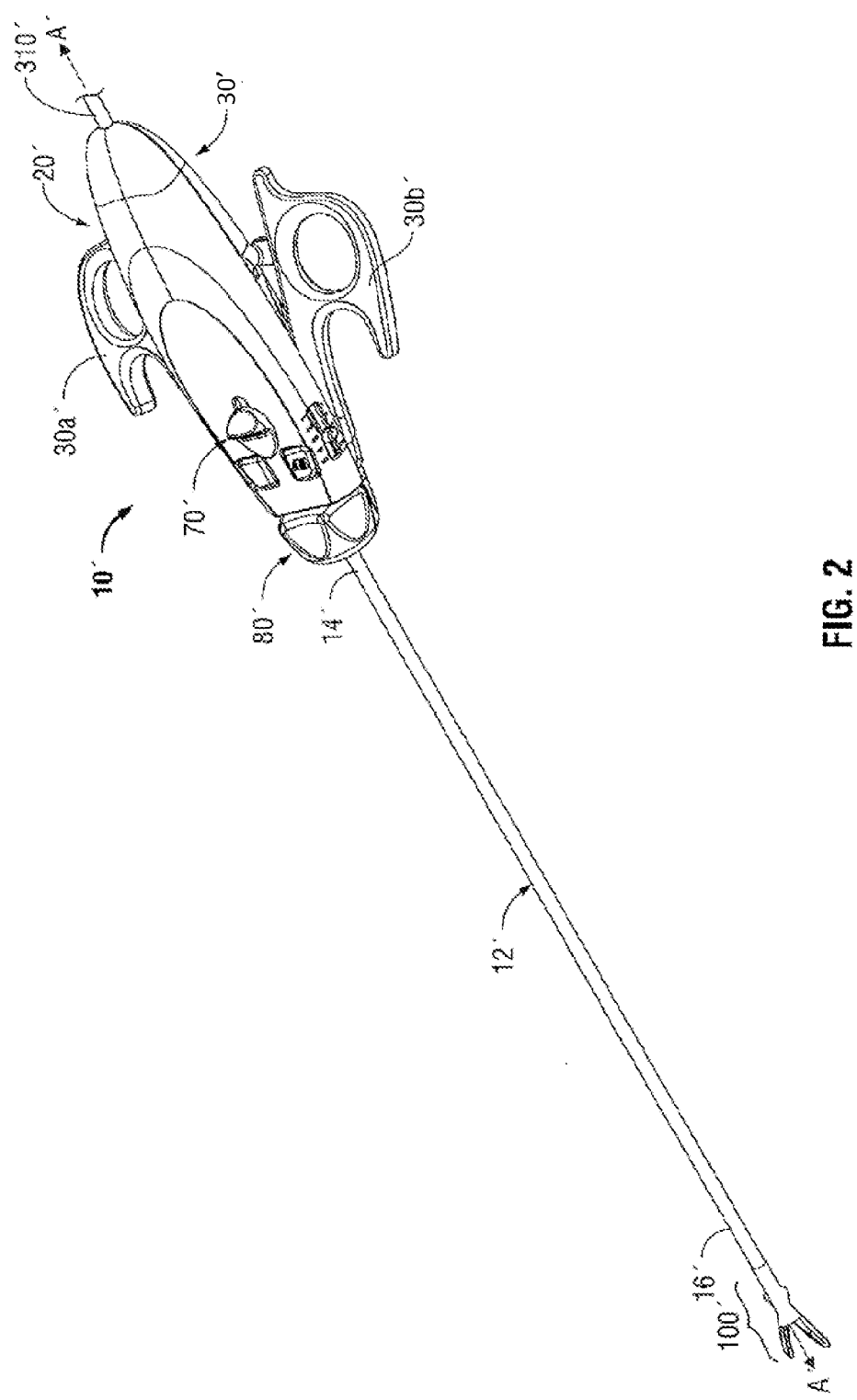
FIG. 2 is a top, perspective view of an endoscopic forceps shown in an open configuration and including a housing, a handle assembly, a shaft and an end-effector assembly for use with the present disclosure.

Turning now to FIG. 2, an endoscopic surgical forceps 10' is shown for use with various surgical procedures and generally includes a housing 20', a handle assembly 30', a rotating assembly 80', a knife trigger assembly 70' and an end-effector assembly 100' which mutually cooperate to grasp, seal and divide tubular vessels and vascular tissue.

Forceps 10' includes a shaft 12' that has a distal end 16' dimensioned to mechanically engage the end-effector assembly 100' and a proximal end 14' that mechanically engages the housing 20'. The proximal end 14' of shaft 12' is received within the housing 20'. Forceps 10' also includes an electrosurgical cable 310' that connects the forceps 10' to a source of electrosurgical energy, e.g., a generator (not explicitly shown). Handle assembly 30' includes two movable handles 30a' and 30b' disposed on opposite sides of housing 20'. Handles 30a' and 30b' are movable relative to one another to actuate the end-effector assembly 100'.

Rotating assembly 80' is mechanically coupled to housing 20' and is rotatable approximately 90 degrees in either direction about a longitudinal axis "A" defined through shaft 12'. Rotating assembly 80', when rotated, rotates shaft 12', which, in turn, rotates end-effector assembly 100'. Such a configuration allows end-effector assembly 100' to be rotated approximately 90 degrees in either direction with respect to housing 20'. Details relating to the inner-working components of forceps 10' are disclosed in commonly-owned U.S. Pat. No. 7,789,878, the entire contents of which is incorporated by reference herein.

Figure 3:
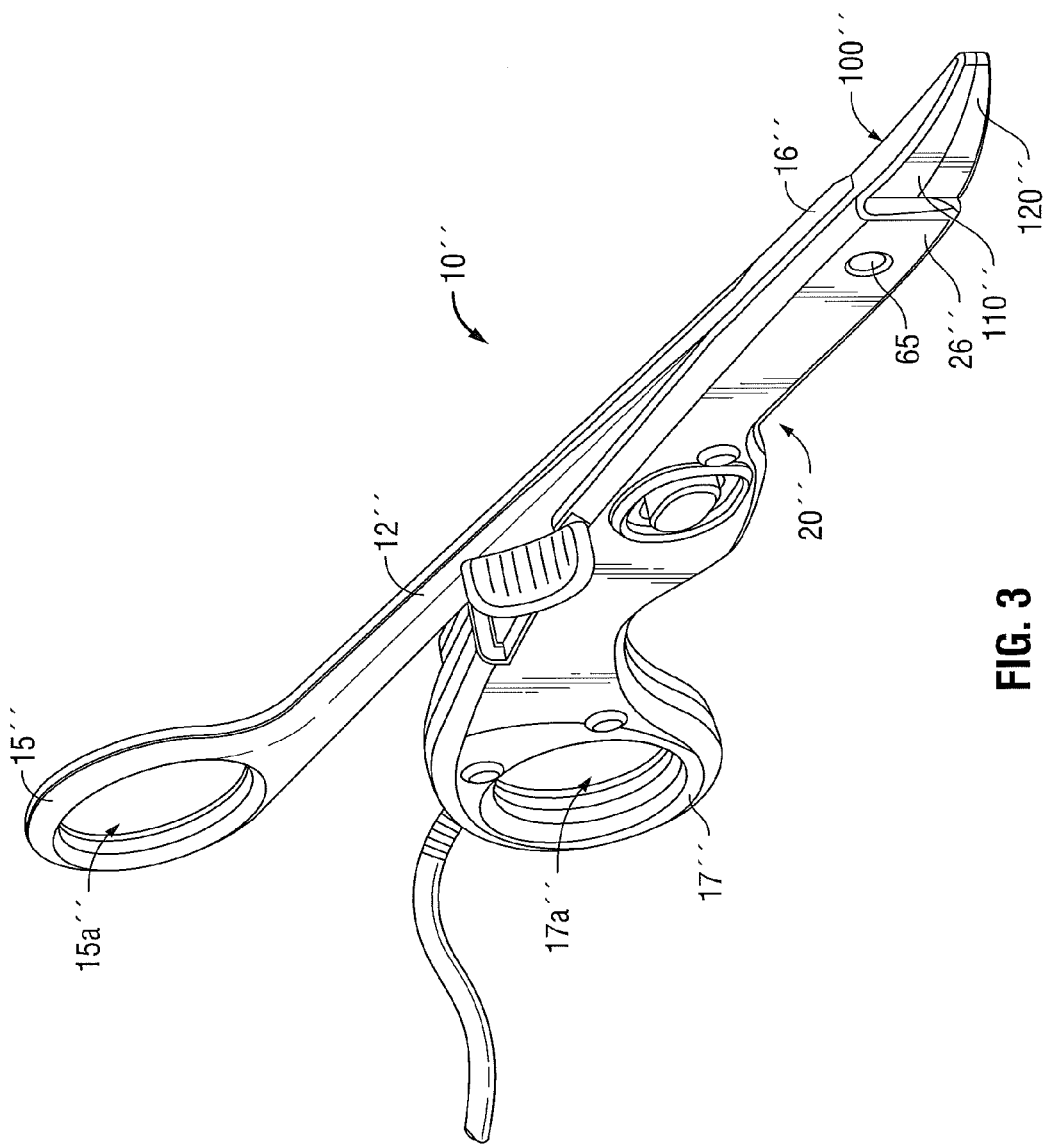
FIG. 3 is a top, perspective view of an open surgical forceps, including a handle assembly, first and second shafts and an end-effector assembly for use with the present disclosure.

Referring now to FIG. 3, another alternate embodiment of a forceps 10" for use with open surgical procedures is shown. Forceps 10" includes end-effector assembly 100" that attaches to distal ends 16" and 26" of shafts 12" and 20", respectively. The end-effector assembly 100" includes a pair of opposing jaw members 110" and 120" which are pivotably connected about a pivot pin 65 and that are movable relative to one another to grasp tissue therebetween.

Each shaft 12" and 20" includes a handle 15" and 17", disposed at the proximal end thereof which each define a finger hole 15a" and 17a", respectively, therethrough for receiving a finger of the user. As can be appreciated, finger holes 15a" and 17a" facilitate movement of the shafts 12" and 20" relative to one another which, in turn, pivot the jaw members 110" and 120" from an open position wherein the jaw members 110" and 120" are disposed in spaced relation relative to one another to a clamping or closed position wherein the jaw members 110" and 120" cooperate to grasp tissue therebetween. End-effector assembly 100" is configured in a similar manner to the end-effector assembly of FIGS. 1 and 2 above.

Figure 4:
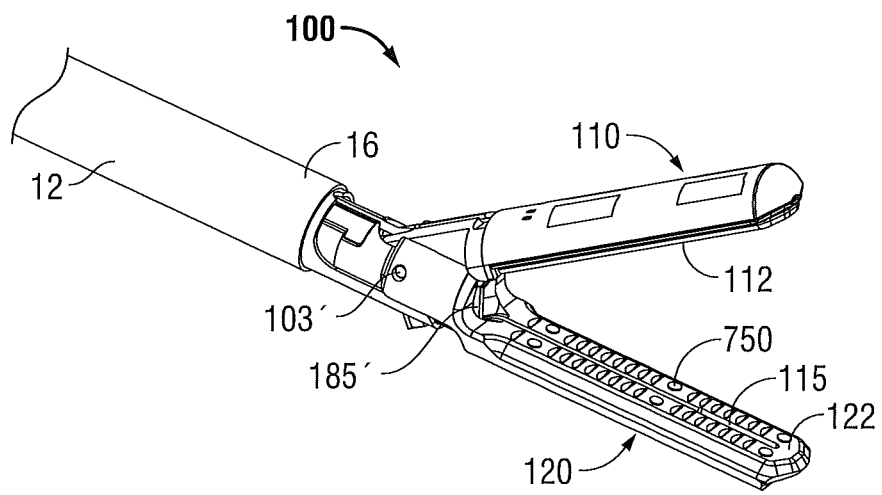
FIG. 4 is an enlarged, side, perspective view of the end-effector assembly of FIG. 1.

Referring now to FIG. 4, end-effector assembly 100 is described with reference to the end-effector assembly 100 show in FIG. 1. It is understood that all of the above end effector assemblies and forceps include similar designs and may be configured to accomplish the same purpose. End-effector assembly 100 may be configured for mechanical attachment at the distal end 16 of shaft 12 of forceps 10. End-effector assembly 100 includes a pair of opposing jaw members 110 and 120. Handle assembly 30 of forceps 10 (see FIG. 1) ultimately connects to a respective drive assembly (not shown) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween. Details relating to the working components of the handle assembly and drive assembly of forceps 10 are disclosed in above-mentioned U.S. Pat. No. 7,789,878.

With reference to the example embodiment of an end-effector assembly 100 shown in FIG. 4, opposing jaw members 110 and 120 are pivotably connected about pivot 103'. Jaw members 110 and 120 include electrically conductive sealing surfaces 112 and 122 that are dimensioned to securely engage tissue when clamped therebetween. A longitudinally-oriented knife channel 115 is defined between jaw members 110 and 120 for reciprocation of knife 185' therethrough. Knife channel 115 is defined by channels 115a and 115b (see, e.g., FIGS. 5A-5B) disposed in the sealing surfaces 112 and 122, respectively. Alternatively, knife channel 115 may be defined completely within one of the sealing surfaces 112 and 122. Further, forceps 10 may be provided without the knife assembly and, accordingly, the sealing surfaces 112 and 122 would be configured without the knife channel 115 defined therethrough. At least one of the jaw members 110, 120 may include an electrically insulative stop member (or members) 750 configured to control the gap distance between sealing surfaces 112 and 122 of jaw members 110 and 120, respectively.

Figure 5A:
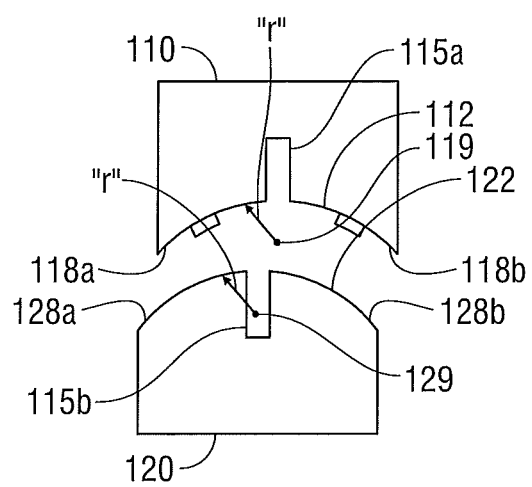
FIG. 5A is a front, cross-sectional view of the jaw members in an open configuration in accordance with one embodiment of the present disclosure.

Features of jaw members 110 and 120 will now be described with reference to FIGS. 5A-5B and 6A-6B. FIG. 5A shows jaw members 110 and 120 disposed in a first, spaced-apart position. Sealing surface or opposing surface 112 of jaw member 110 has a generally concave shape. Sealing surface or opposing surface 122 of jaw member 120 has a generally convex shape. More specifically, sealing surface 112 defines an inward radial portion from opposite longitudinal sides 118a and 118b of sealing surface 112 having a radius "r" from a center point 119 of sealing surface 112. Opposing sealing surface 122 defines an outwardly protruding convex portion extending from opposite longitudinal sides 128a and 128b of sealing surface 122 and having a radius "r" from a center point 129 of sealing surface 122, which is substantially equal to the radius "r" of the radial portion defined within jaw member 110. Accordingly, opposing surface 112 and opposing surface 122 have complementary and, preferably non-linear shapes such that when the jaw members 110 and 120 are moved into the second, or closed position, the concave radial portion of jaw member 110 and the convex radial portion of jaw member 120 fit together, as shown in FIG. 5B.

These complementary-shaped opposing surfaces 112 and 122 of FIGS. 5A-5B align the jaw members 110 and 120 as described hereinbelow. For example, as shown in FIG. 5A, due to the inherent splay which results when two surfaces connected about a pivot come together, jaw members 110 and 120 may be offset from one another as the jaw members 110 and 120 move to and from open and closed positions. For example, as shown in FIG. 5A, jaw member 110 is offset relative to jaw member 120. As jaw members 110 and 120 move to the position shown in FIG. 5B, jaw member 110 is forced into alignment with jaw member 120, so that the complementary opposing surfaces 112 and 122 fit together.

Further, the self-aligning feature of the above-described complementary-shaped opposing surfaces 112 and 122 ensures alignment of knife channels 115a and 115b as jaw members 110 and 120 move from an open to a closed position. The alignment of knife channels 115a and 115b, as shown in FIG. 5B, allows knife blade of knife 185' (see FIG. 4) to more easily translate through knife channel 115 to cut tissue disposed between jaw members 110 and 120. Additionally, the complementary concave and convex sealing surfaces 112 and 122, respectively, provide a larger seal width as compared to linear sealing surfaces having the same overall width. On the other hand, the complementary concave and convex sealing surfaces 112 and 122, respectively, allow jaw members 110 and 120 to be constructed with an overall smaller width, while maintaining an equal seal width as compared to jaw members having linear sealing surfaces.

Figure 5B:
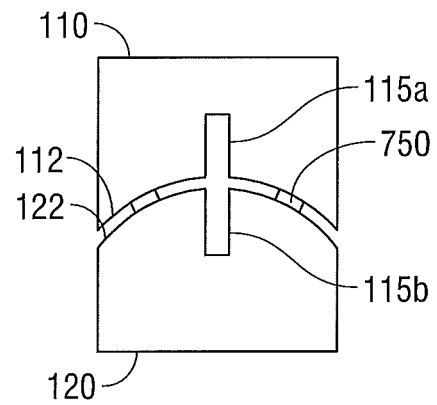
FIG. 5B is a front, cross-sectional view of the jaw members of FIG. 5A, disposed in a closed configuration.

The vessel sealing instruments illustrated in FIGS. 1-3, with end effectors similar to the end effectors illustrated in FIGS. 4, and 5A-5B, are three examples of a family of surgical instruments used for tissue fusion. Other tissue fusion devices may not include a cutting apparatus, may be configured to spot fuse tissue of particular tissue (e.g., fusing nerve tissue) or may be configured to perform tissue fusion along a resection line.

Normally, tissue fusion cannot be performed in a surgical field with electrically conductive fluid. In use, a clinician must be aware of fluid in the surgical field, as an electrosurgical generator (not explicitly shown) will normally detect such conditions and will fail to perform, or even start, the electrosurgical energy delivery algorithm if the surgical instrument detects contact with electrically conductive fluid.

Other electrosurgical instruments that normally perform electrosurgical procedures in a fluid-filled surgical field (e.g., prostantectomy's, fibroid removals in the uteruses and urinary bladder ablations) typical favor instruments based on an ablative electrosurgical algorithm.

Figure 6A:
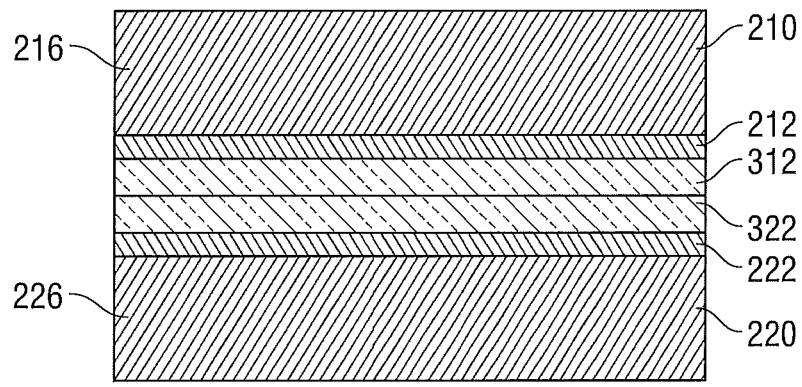
FIG. 6A is a side, cross-sectional view of a portion of the jaw members disposed in a closed configuration with a compressible membrane in accordance with one aspect of the present disclosure.
Figure 6B:
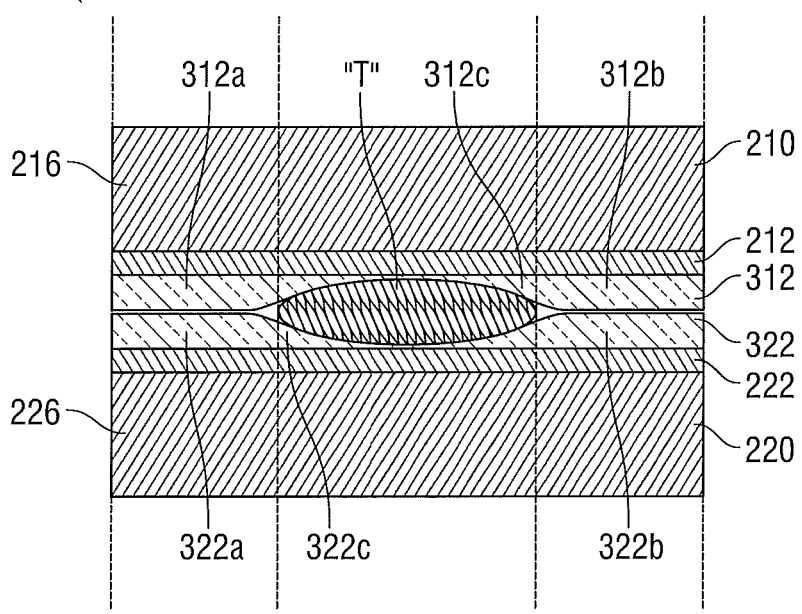
FIG. 6B is a side, cross-sectional view of a portion of the jaw members disposed in a closed configuration with a compressible membrane with tissue positioned between the jaw members.

One aspect of the present disclosure positions a compressible membrane 312, 322 in the conventional jaw arrangement of the end effectors provided in FIGS. 1-4 and 5A-5B thereby minimizing (and possibly eliminating) leakage currents due to the presence of electrically conductive fluids in the surgical field or leakage currents due to contact with tissue adjacent the target tissue. FIGS. 6A and 6B illustrate a partial cross-section of a portion of an end effector assembly 200 with opposing jaw members 210 and 220 according to one aspect of the present disclosure. Each jaw member 210, 220 includes a jaw housing 216, 226 that houses a jaw conductive plate 212, 222 that each connect to opposing potentials of a source of electrosurgical energy (e.g., electrosurgical generator, not explicitly shown).

Compressible membranes 312, 322 cover the outward facing portion of respective jaw conductive plates 212, 222. In one aspect, the compressible membranes 312, 322 completely cover the outward surfaces of respective jaw conductive plates 212, 222 thereby preventing any direct contact between the jaw conductive plates 212, 222 and tissue "T" and/or fluid in the surgical field. Each compressible membrane 312, 322 connects to the source of electrosurgical energy through the respective jaw conductive plate 212, 222.

The compressible membranes 312, 322 include one or more properties, features and/or other aspects that provide a change in impedance and/or resistance when compressed. The change may be due to (or related to) a physical change in structure. For example, an applied compression bias, due to the tissue "T" positioned between the jaw members 210, 220, may deform the shape of the compressible membranes 312, 322 wherein the deformation results in a change in impedance and/or resistance. Alternatively, the change may be due to the applied compression bias, which may not result in a dimensional/physical change in the compressible membranes 312, 322. For example, the tissue "T" positioned between the jaw members 210, 220 may not substantially deform the compressible membrane 312, 322 although the applied compression bias (due to the tissue "T") may change the impedance and/or resistance of the compressible membrane 312, 322 at the location of the compression bias (at the tissue "T").

A change in the physical structure of the compressible membranes 312, 322 may be due to compression of the compressible membranes 312, 322 or due to redistribution of the material in the compressible membranes (See compressible membranes 412, 422, 512, 522). For example, the compression bias may reduce the thickness of the compressible membrane 312, 322 in the area where the compression bias is applied, while the thickness of the remaining portion of the compressible membranes (312, 322) remains substantially unchanged. Alternatively, the applied compression bias may result in a redistribution of the material that forms the compressible membrane. As such, the thickness of the compressible membrane 312, 322 may be reduced in the area where the compression bias is applied while the thickness of the remaining portion of the compressible membrane 312, 322 may increase.

A compressible membrane 312, 322 that changes structure may conform to the contours (e.g., shape) of the tissue "T". The varying contours and thickness of the tissue "T" may result in an impedance geometry that is related to the geometry of the tissue "T".

In another aspect of the present disclosure, the applied compression bias generated by compressing the tissue "T" between the jaw members 210, 220 may change the impedance of the compressible membrane 312, 322 without changing the shape, structure or distribution of material of the compressible membrane 312, 322.

As illustrated in FIG. 6A, the thickness of the compressible membranes 312, 322 in an uncompressed condition is substantially uniform along the length of the jaw members 210 and 220. While not explicitly shown, the thickness of the compressible membranes 312, 322 may also be substantially uniform along the width of the jaw members 210, 220. Further, each of the compressible membranes 312, 322 may include a compressible membrane formed on each side of respective knife channels 115a, 115b (See FIGS. 4, 5A and 5B). The compressible membranes 312, 322 in an uncompressed condition form a high-impedance barrier between the surgical field and the jaw conductive plates 212, 222 as discussed in more detail hereinbelow.

As illustrated in FIG. 6B, at least a portion of each compressible membrane 312 and 322 is compressed by tissue "T" positioned between the jaw members 210 and 220. The uncompressed portions 312a-312b and 322a-322b of the compressible membranes 312 and 322 maintain a high-impedance barrier and the compressed portions 312c and 322c of the compressible membranes 312 and 322 form an area of variable impedance. The impedance in the uncompressed portions 312a-312b and 322a-322b is much higher than the tissue goal impedance within the compressed portions 312c, 322c (e.g., the tissue goal impedance is the combined impedance of the impedance of the compressed portions 312c and 322c and the impedance of the tissue at any point in time during the sealing procedure).

The variable and varying impedance of the compressed portions 312c and 322c along the length and width of the tissue "T" steers electrical currents to low impedance pathways through tissue "T". As such, the current density pattern formed in the tissue "T" may be related to the impedance of the tissue "T" and the amount of compression and/or the amount of compression bias applied to the compressible membrane 312, 322 along each point of the tissue "T".

In one aspect of the disclosure, the compressible membranes 312, 322 form a variable capacitor. In an uncompressed condition, the capacitance of the compressible membranes 312, 322 is very low. In a compressed condition, the compressible membranes 312, 322 have a higher capacitance and can act much like a capacitor. A capacitor is formed by positioning two parallel conductive surfaces in parallel and separated by a dielectric. Assuming that the dielectric constant remains the same, the capacitance of a capacitor increases as the distance between the surfaces decreases. The variability of capacitance is represented as:

$$C = \varepsilon_r \varepsilon_0 \frac{A}{d} \quad (1)$$

where,

C is the capacitance between two parallel conductive plates (in farads), A is the area of overlap between the two parallel plates measured in square meters, $\varepsilon_r$ is the relative static permittivity of the membrane between plates, $\varepsilon_o$ is the permittivity of free space (where $\varepsilon_o$=8.854×10$^{-12}$ F/m) and d is the separation between the plates, measured in meters. As shown in Equation 1, capacitance is directly proportional to the surface area of the conductive plates or sheets.

The starting impedance (hereinafter, "$Z_{start}$") for tissue in a surgical procedure is typically very low and almost entirely resistive (as opposed to capacitive or inductive). For example, $Z_{start}$ may be less than about 50 ohms.

The goal impedance (hereinafter, "$Z_{goal}$") for tissue in a surgical procedure is typically at least 10 to 100 times greater than $Z_{start}$ and only partly resistive. For example, $Z_{goal}$ may be as much as 5000 ohms.

The frequency of RF energy in a surgical procedure may be in the range of 100 kHz to 1000 kHz, with a typical frequency of about 472 kHz generating AC currents in the range from a few milliamps to several amps (as much as 5 amps).

Figure 7:
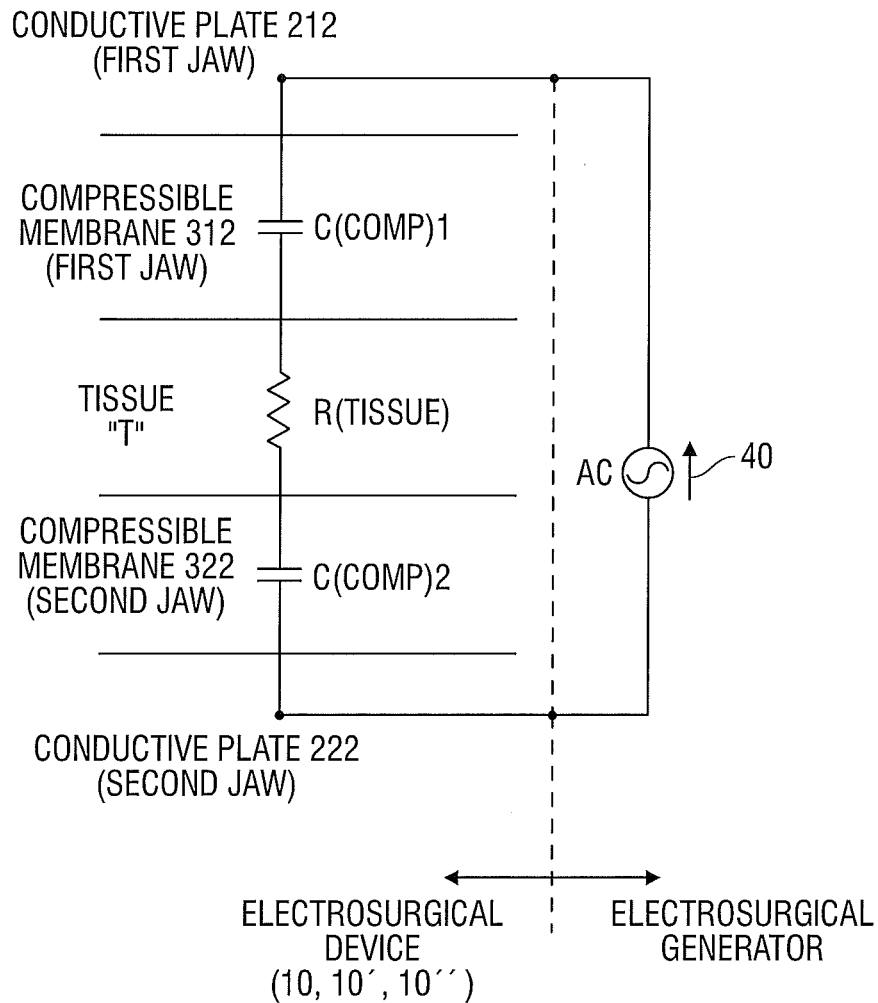
FIG. 7 is an electrical circuit schematic that approximates the electrical circuit formed by the end effector of FIG. 6B.

The arrangement of the opposing jaws 210 and 220, and in particular the jaw conductive plates 212 and 222 and the compressible membranes 312 and 322, form an electrical circuit through tissue, as illustrated in the first approximation circuit of FIG. 7.

The first approximation circuit is a series circuit that includes the capacitance of the first jaw compressible membrane 312, $C_{(comp)}1$, the resistance of the tissue "T", $R_{tissue}$, and the capacitance of the second jaw compressible membrane 322 $C_{(comp)}2$ connected in series to the electrosurgical generator "AC". From the perspective of the electrosurgical generator "AC", the capacitors are directly in series. Assuming that $C_{(comp)}1$ is approximately equal to $C_{(comp)}2$, the mathematical model of the generator load impedance of this circuit is as follows:

$$Z_{load} = Z_{C(comp)1, C(comp2)} + R_{(tissue)} \quad (2)$$

$$Z_{load} = \frac{1}{j\omega \frac{C_{(comp)1} * C_{(comp)2}}{C_{(comp)1} + C_{(comp)2}}} + R_{(tissue)} \quad (3)$$

$$Z_{load} = \frac{1}{j\omega \frac{C_{(comp)}}{2}} + R_{(tissue)} \quad (4)$$

Since the normal process for tissue fusion begins with a low tissue impedance, it is desirable for the impedance due to the compressible membrane 312 and 322 (when compressed) to also be as low as possible and ideally about equal to or slightly greater than the tissue impedance.

$$R_{tissue} = Z_{start} \geq Z_{C(comp)} \quad (5)$$

$$\frac{1}{j\omega \frac{C_{(comp)}}{2}} \leq Z_{start} \quad (6)$$

$$\frac{1}{j\omega Z_{start}} \leq \frac{C_{(comp)}}{2} \quad (7)$$

This leads to a minimum value of the compressed compressible membrane 312 and 322 capacitance, $C_{(comp)}$, which is determined by the following equation:

$$C_{comp} \geq \frac{2}{j\omega Z_{start}} \quad (8)$$

Figure 8:
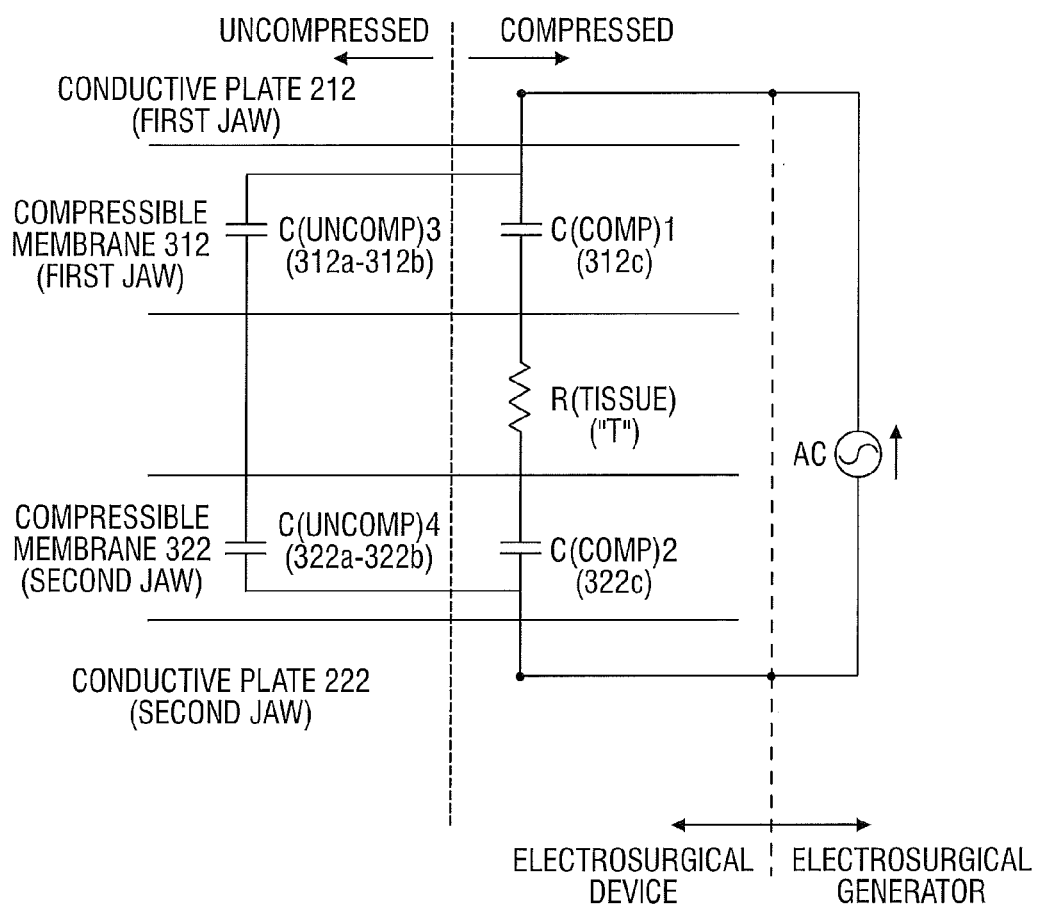
FIG. 8 is an electrical circuit schematic that approximates the electrical circuit formed by the end effector of FIG. 6B including the compressed and uncompressed portions of the compressible membrane.

A second approximation circuit illustrated in FIG. 8, accounts for additional areas of the compressible membrane 312 and 322. In the second approximation circuit the capacitance of the compressible membrane 312 and 322 represents the area of the plates of the capacitor and is related to the combined capacitance of the uncompressed portions 312a-312b, 322a-322b and the compressed portions 312c, 322c as well as the distance between the plates (e.g., thickness of the compressible membrane 312, 322).

The capacitance of the compressed portion 312c, 322c of the compressible membrane 312 and 322 (e.g., in the area of the tissue) is affected by the compression bias while the capacitance of the uncompressed portions 312a-312b and 322a-322b (e.g., the area outside of the tissue "T") of the compressible membrane 312a-312b and 322a-322b is not affected by the compression bias. As such, the capacitance of uncompressed portions 312a-312b and 322a-322b ($C_{uncomp}4$ and $C_{uncomp}4$, respectively) of the compressible membrane 312, 322 with respect to the compressed portion 312c, 322c ($C_{(comp)}1$ and $C_{(comp)}2$, respectively) of the compressible membrane 312 and 322 may be represented as follows:

$$Z_{load} = \frac{Z_{uncomp} * (Z_{comp} + R_{tissue})}{Z_{uncomp} + (Z_{comp} + R_{tissue})} \quad (9)$$

Where $Z_{uncomp}$ is a series capacitive circuit modeled as:

$$Z_{uncomp} = \frac{1}{j\omega * \frac{C_{uncomp3} * C_{uncomp3}}{C_{uncomp3} + C_{uncomp3}}} \quad (10)$$

Again, $C_{uncomp}3$ is substantially equal to $C_{uncomp}4$ thereby reducing equation 9 as follows:

$$\frac{1}{j\omega * \frac{C_{uncomp}}{2}} = Z_{uncomp} \quad (11)$$

At the tissue goal impedance, $Z_{goal}$, $Z_{comp}$ is a negligible factor compared to $R_{tissue}$, therefore, the circuit reduces to two parallel impedances, $Z_{uncomp}$ and $R_{tissue}$. As discussed hereinabove, the uncompressed membrane impedance is much higher than the goal impedance of the tissue by at least a factor of 10 although higher ratios are clearly acceptable and/or desirable.

$$\frac{1}{j\omega * \frac{C_{uncomp}}{2}} = Z_{uncomp} \geq 10 * Z_{goal} \quad (12)$$

$$C_{uncomp} \leq \frac{1}{j\omega * 5 * Z_{goal}} \quad (13)$$

As can be appreciated, increasing the amount of tissue "T" positioned between the jaw members 210 and 220 decreases the amount (e.g., total surface area) of the uncompressed portion 312a-312b and 322a-322b of the compressible membrane 312 and 322 thereby reducing the capacitance of the compressed portion of the compressible membrane 312, 322. As a result, more current is steered into the tissue "T" as long as the maximum capacitance for the uncompressed area is maintained.

Figure 9:
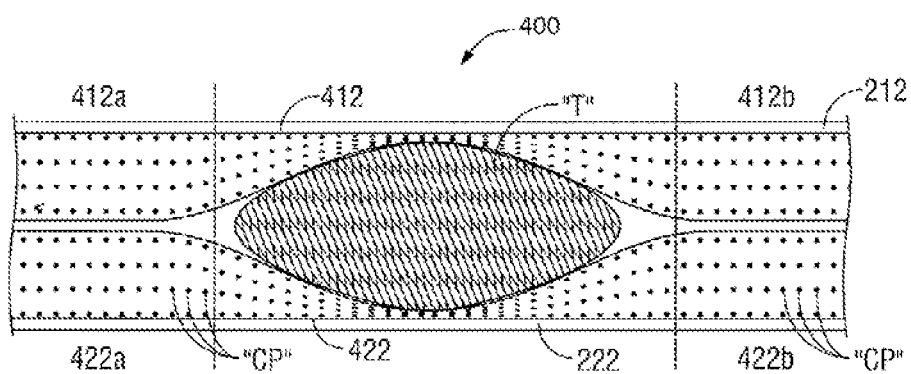
FIG. 9 is a side, cross-sectional view of a portion of a jaw member with another aspect of a compressible member of the present disclosure, with tissue positioned between the jaw members.
Figure 10:
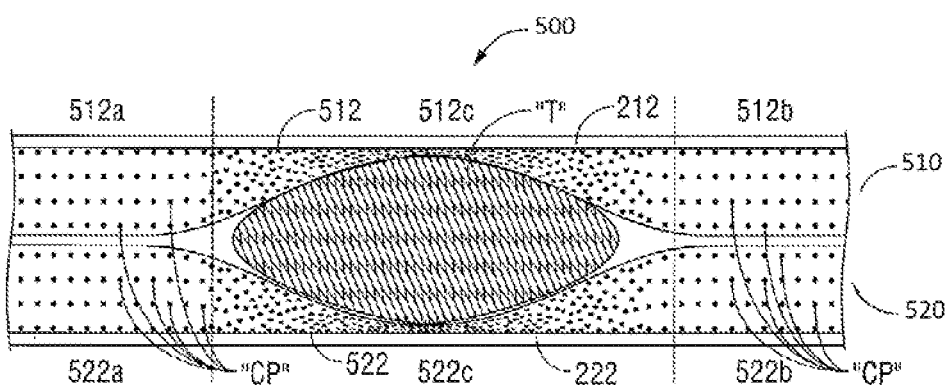
FIG. 10 is a side, cross-sectional view of a portion of a jaw member with yet another aspect of a compressible member of the present disclosure, with tissue positioned between the jaw members.
Figure 11:
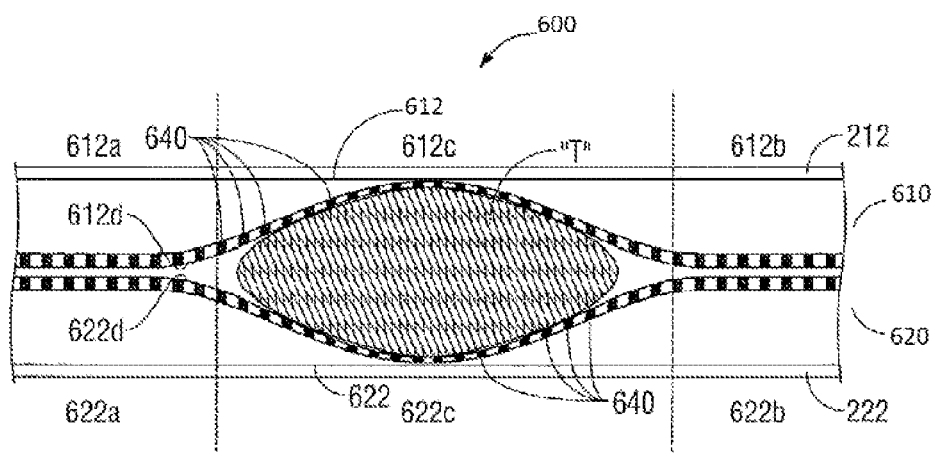
FIG. 11 is a side, cross-sectional view of a portion of a jaw member with yet another aspect of a compressible member including a plurality of switches formed in the compressible membranes.

As discussed hereinabove, other material properties may be exploited to practice the fundamentals of the present disclosure. FIGS. 9-11 illustrate additional embodiments of the present disclosure.

FIG. 9 illustrates a partial cross-section of an end effector assembly 400 that includes opposing jaw members 410 and 420. Each jaw member 410, 420 include a jaw conductive plate 212, 222 and compressible membranes 412, 422. The jaw conductive plates 212, 222 connect to opposing potentials of a source of electrosurgical energy (e.g., electrosurgical generator, not explicitly shown) and provide electrosurgical energy to the corresponding compressible membrane 412, 422 attached thereto.

Compressible membranes 412 and 422, instead of having a variable capacitance, as discussed hereinabove with respect to FIGS. 7 and 8, each include an array of conductive particles "CP" embedded through-out each of the compressible membranes 412 and 422. Compression of the compressible membranes 412 and 422 decreases the distance between the conductive particles "CP" thereby changing the conductive properties of the compressible membranes 412 and 422.

In one embodiment, the conductivity of the compressible membrane 412, 422 is related to the percentage of the compression. For example, as a portion of the compressible membrane 412, 422 is compressed, the distance between conductive particles "CP" decreases and the compressed portion of the compressible material 412, 422 becomes more conductive. The percentage of compression may range from about 0% compression (e.g., uncompressed) to 90% compression, wherein the thickness at 90% compression is about $\frac{1}{9}^{th}$ the thickness at 0% compression. The compression percentage is related to the conductivity of the compressible membrane 412, 422 wherein the conductivity decreases with an increase in the compression percentage.

The change in conductivity of the compressible membrane 412, 422 may be directly proportional to the compression percentage (e.g., related to the change in thickness). This relationship may be a linear or a non-linear relationship with respect to the compression percentage.

The conductivity of the compressible membrane 412, 422 may be related to a change in the spacing between the conductive particles "CP" or related to a change in the distribution of the conductive particles "CP". The relationship therebetween may be a linear, a non-linear or any combination thereof.

The cross-sections illustrated in FIGS. 9 and 10 exposes a particular distribution of conductive particles "CP" formed in the compressible membranes 412, 422. The particular distributions are exemplary as any suitable particle distribution may be used. The uncompressed portions 412a-412b and 422a-422b of the compressible membrane 412 and 422, respectively, illustrate evenly distributed conductive particles "CP" with substantially uniform spacing between columns and/or rows.

In FIG. 9, a varying compression bias is applied to the compressible membranes 412, 422 in the area adjacent tissue "T" wherein the force of the compression bias is related to the thickness of the tissue "T" positioned between the compressible membranes 412, 422. As the compression bias applied by the tissue "T" increases, the spacing between the rows of the conductive particles "CP", within the compressible membranes 412, 422, is reduced while the spacing between the columns of conductive particles "CP" remains unchanged. In other words, under compression the arrangement of the conductive particles "CP" remains substantially the same with respect to the spacing between columns with the only change in the arrangement of the conductive particles "CP" being a decrease in the spacing between rows. In this particular embodiment, applying a compression bias to the compressible membrane 412, 422 does not redistribute the conductive particles "CP" but merely changes the spacing therebetween.

In a further embodiment, at least one of the compressible membranes 412, 422 exhibits resilient properties wherein a substantial portion of the compressible membrane 412, 422 returns to its original shape (e.g., thickness and/or material distribution) after the compression bias is removed.

FIG. 10 illustrates another embodiment of the present disclosure wherein a varying compression bias applied by the tissue "T" results in a redistribution of the conductive particles "CP". As illustrated in the cross-section of FIG. 10, a particular distribution of conductive particles "CP" is formed in the compressible membranes 512, 522 of an end effector assembly 500. The end effector assembly includes opposing jaw members 510 and 520 each jaw member 510, 520 including a jaw conductive plate 212, 222 and a compressible membrane 512, 522. The jaw conductive plates 212, 222 each connect to opposing potentials of a source of electrosurgical energy (e.g., electrosurgical generator, not explicitly shown) and provide electrosurgical energy to the corresponding compressible membrane 512, 522 attached thereto.

The uncompressed portions 512a-512b and 522a-522b of the compressible membranes 512 and 522, respectively, illustrate evenly distributed conductive particles "CP" with substantially uniform spacing between columns and between rows. As a compression bias is applied to the compressible membranes 512, 522 (e.g., in the area adjacent tissue "T") the spacing between conductive particles "CP" within the compressible membranes 512, 522 is reduced with respect to the spacing between rows of conductive particles "CP" and with respect to the spacing between columns of conductive particles "CP". In other words, applying a compression bias to the compressible membrane 512, 522 changes the spacing between the conductive particles "CP" in the compressed portion 512c, 522c of the compressible membranes 512, 522 by redistributing and/or repositioning the conductive particles "CP". As such, the change in the conductive property of the compressible membranes 512, 522 may be due to the change in the distance between conductive particles "CP" (due to the applied compression bias), may be due to the redistribution of the conductive particles "CP" or both.

In one embodiment, the compressible membranes 512, 522 includes a gel-like material that is repositionable within the compressible membranes 512, 522. The varying compression bias, applied to the compressible membranes 512, 522 by compressing the tissue "T", repositions the gel-like material within the compressible membranes 512, 522. Repositioning of the gel-like material may change one or more material properties, such as, for example, the repositioning may decrease the capacitance and/or the resistance of in the vicinity of the applied compression bias (e.g., in the area adjacent tissue "T"). The repositioning of the gel-like material may also increasing the capacitance and/or the resistance of the uncompressed portions 512a-512b and 522a-522b of the compressible membranes 512, 522 in the vicinity away from the applied compression bias. Alternatively, repositioning the gel-like material may increase the conductive properties of the compressible membranes 512, 522 in the vicinity of the applied compression bias while the repositioned material may decrease the conductive properties in the vicinity of the uncompressed portion 512a-512b and 522a-522b.

FIG. 11 illustrates another embodiment of the present disclosure in which the cross-section exposes a plurality of switching mechanisms 640 embedded in or near the opposing surfaces of one or both compressible membranes 612, 622. The end effector assembly 600 includes opposing jaw members 610 and 620 that each include a jaw conductive plate 212, 222 and a compressible membrane 612, 622. The jaw conductive plates 212 and 222 connects to opposing potentials of a source of electrosurgical energy (e.g., electrosurgical generator, not explicitly shown), and provides electrosurgical energy to each of the corresponding compressible membrane 612, 622 attached thereto.

The compressible membranes 612, 622 may include a plurality of switches 640 formed on, or below, one or more opposing surfaces 612d, 622d. Switches 640, in the absence of an applied compression bias, form a high-resistance pathway (e.g., form an open connection) through the compressible membranes 612, 622. As such, the uncompressed portions 612a-612b and 622a-622b of the respective compressible membrane 612, 622 form a high-resistance and/or low conduction pathway between the jaw conductive plates 212 and 222.

The application of a compression bias (e.g., positioning of tissue "T" between the compressible membranes 612, 622) engages individual switches 640 thereby forming a plurality of low resistance connections with tissue "T" and the portions of the compressible membranes 612, 622 receiving the compression bias. As such, the compressed portions 612c, 622c form a low-resistance and/or a highly conductive pathway between the jaw conductive plates 212, 222 through the compressed portions 612c and 622c of the compressible membranes 612 and 622 and the tissue "T" positioned therebetween.

Figure 12:
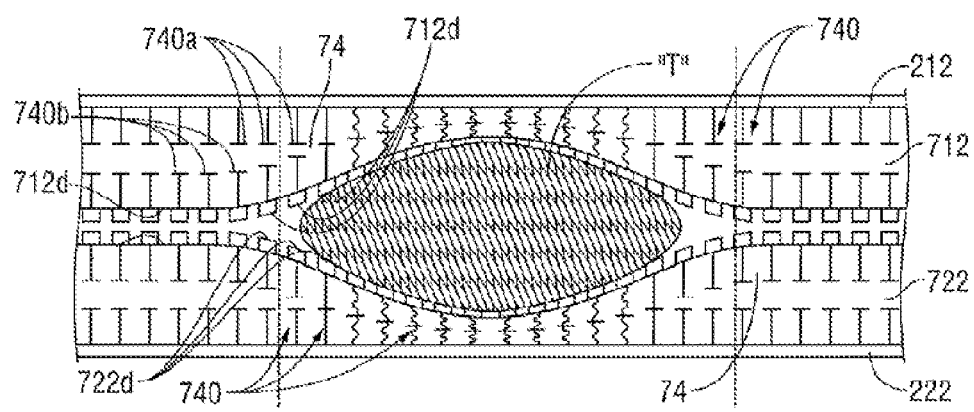
FIG. 12 is a side, cross-sectional view of a portion of a jaw member with yet another aspect of the compressible member including a plurality of parallel plates formed in each of the compressible membranes.

FIG. 12 illustrates another embodiment of the present disclosure in which the cross-section exposes a plurality of switches 740 each including an inner plate 740a and a corresponding outer plate 740b positioned in the compressible membranes 712 and 722 and separated by a non-conductive fluid 74. The inner plates 740a individually connect to the respective jaw conductive plate 212, 222 and the outer plates 740b individually connect to the opposing surfaces 712d and 722d of the respective compressible membranes 712 and 722. In an uncompressed condition, each inner plate 740a and outer plate 740b pair is separated by the non-conductive fluid thereby forming a high-resistance and/or low conduction pathway through the compressible membranes 712, 722. The application of a compression bias compresses the compressible membranes 712, 722 thereby moving the inner plates 740a and/or the outer plates 740b toward one another in the vicinity of the applied compression bias (e.g., adjacent the tissue "T"). Moving the upper plates 740a and the lower plates 740b toward one another forces the non-conductive fluid 74 from between the individual pairs of upper and lower plates 740a and 740b and at least a portion of the upper and lower plates 740a and 740b form an electrical connection therebetween.

The compression bias generated by compressing tissue "T" must overcome the fluid pressure formed within the compressible membranes 712, 722 to displace the non-conductive fluid 74 from between the parallel plates 740a and 740b. Displacing the non-conductive fluid 74 and forcing the parallel plates 740a and 740b together forms a low-resistance and/or highly conductive pathway between the jaw conductive plates 212 and 222 through the compressible membranes 712, 722 and the tissue "T".

Various aspects described in the present disclosure effectively "steer" or "direct" current to the portions of the compressible membranes where the tissue applies a compression bias between the jaw members 210, 220 thereby reducing, if not eliminating, stray current paths that are not through tissue "T". Eliminating and/or reducing stray currents reduces the overall energy requirements of the electrosurgical generator, improves electrosurgical generator efficiently and increases patient safety.

The compressible membranes described herein may include a fluid with viscous properties that facilitate the deformation of the compressible membranes adjacent tissue "T". In one embodiment, the viscosity of the fluid in the compressible membrane is indirectly proportional to temperature (e.g., an increase in temperature decreases the viscosity of the fluid). As such, heat generated in tissue "T" conducts to a portion of the compressible membrane adjacent the tissue "T" thereby lowering the viscosity of the fluid in the compressible membrane. Lowering the viscosity of the fluid adjacent the tissue "T" may provide additional compression of the compressible membrane.

Fluid in the compressible membrane may be configured to expand as temperature increases. Expansion of the fluid in the compressible membrane increases the pressure applied to the tissue "T" positioned between. At the initiation of a seal cycle, the temperature of the compressible membrane is at a minimum. As the sealing cycle is performed, the temperature of the compressible membrane increases thereby resulting in an expansion of the fluid that forms the compressible membrane. The expansion results in an increase in the pressure applied to tissue "T" and binding of the collagen/elastin is performed under the higher pressures. The tissue "T", as it continues to heat, eventual shrinks thus reducing the pressure applied by the jaw members 210, 220. As such, the pressure profile may be used to determine the completion of the seal cycle.

In some embodiments, the compressible membranes described herein may include a rheopectic fluid wherein the viscosity increases when subjected to the compression bias. Rheopectic fluids show a time-dependent change in viscosity wherein the longer the fluid undergoes a shearing force, the higher its viscosity. Application of a compression bias to a compressible membrane containing a rheopectic fluid increases the viscosity of the fluid. Fluid may be displaced by the placement of tissue "T" between the jaw members 210, 220 (e.g., fluid moves away from the tissue "T" where the pressure is applied) thereby expanding other areas of the jaw members thus resulting in an increased compression bias being applied to the displaced fluid. The rheopectic nature of the fluid would result in an increase in viscosity and possible partial or full solidification of at least a portion of the rheopectic fluid.

In some embodiments, compressible membrane provides a minimum separation distanced (e.g., gap) between the jaw members 210, 220 thereby preventing closure therebetween and preventing pre-mature cutting of the tissue "T". Embodiments that include a rheopectic fluid may form a minimum gap by "setting" (e.g., increasing of viscosity) a portion of the rheopectic fluid to a semi-solid or solid state.

Various aspects of the compressible membranes described in the present disclosure electrically insulate and/or isolate the electrically conductive portions of the jaw members (e.g., the jaw conductive plates 212, 222) from the surgical field. The compressible membranes described herein may be applied to other types of electrosurgical instruments. For example, an electrosurgical pencil may include a compressible membrane according to the present disclosure wherein the surgical pencil only conducts after a suitable amount of pressure is applied to the patient by the electrosurgical pencil. The electrical isolation, connection and switching mechanisms described herein, as applied to the various tissue sealing devices, tissue sealing technologies and electrosurgical devices, enables the devices to be utilized in a field flooded with fluid and/or saline, such as, for example, procedures associated with the uterus, bladder, kidneys and prostate.

In addition, steering the electrosurgical currents to the applied compression bias as discussed hereinabove, enables an electrosurgical generator to utilize algorithms associated with vessel sealing in a surgical field flooded with fluid and/or saline. In the generator, alarms related to excess fluid and/or excess leakage currents may be bypassed and/or eliminated and clinician may not to include the step of clearing fluids from the surgical field prior to performing an electrosurgical tissue sealing procedure, thereby reducing the time of such surgical procedures.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An end-effector assembly, comprising:
   first and second jaw members disposed in opposing relation relative to one another, at least one of the jaw members moveable from an open position to a closed position for grasping tissue between the jaw members, the first jaw member having a first electrically conductive plate disposed thereon and the second jaw member having a second electrically conductive plate disposed thereon;

a first compressible membrane disposed on the first electrically conductive plate and a second compressible membrane disposed on the second electrically conductive plate, the first and second compressible membranes configured to electrically connect the first and second conductive plates to a surgical field when the first and second compressible membranes are subjected to a compression bias; and a plurality of switching mechanisms disposed within each of the first and second compressible membranes, each switching mechanism comprising at least one pair of electrically conductive parallel plates, wherein in an uncompressed condition a non-conductive fluid separates the at least one pair of electrically conductive parallel plates and forms a high-resistance pathway through the compressible membrane, and in a compressed condition the at least one pair of electrically conductive parallel plates connects and forms a low-resistance pathway through the compressible membrane.

2. The end-effector assembly of claim 1, wherein the first and second compressible membranes electrically connect the corresponding first and second electrically conductive plates through the portions of the first and second compressible membranes adjacent the compression bias.

3. The end-effector assembly of claim 1, wherein the first and second compressible membranes form a capacitive connection between the corresponding first and second electrically conductive plates through the portions of the first and second compressible membranes adjacent the compression bias.

4. The end-effector assembly of claim 3, wherein the capacitance of the first and second compressible membranes is configured to vary in magnitude in response to the compression bias.

5. The end-effector assembly of claim 1, wherein the first and second compressible membranes form a resistive connection between the corresponding first and second electrically conductive plates through the portions of the first and second compressible membranes adjacent the compression bias.

6. The end-effector assembly of claim 5, wherein the resistance of the resistive connection through each of the first and second compressible membranes is responsive to the compression bias.

7. The end-effector assembly of claim 1, wherein one plate of at least one pair of electrically conductive parallel plates connects to the first or second electrically conductive plate; of one of the first or second jaw members and the corresponding electrically conductive parallel plate of the at least one pair of electrically conductive parallel plates connects to an outer surface of the respective compressible membrane of the jaw member.

8. The end-effector assembly of claim 1, wherein a viscosity of the non-conductive fluid is related a temperature of the compressible membrane.

9. The end-effector assembly of claim 1, wherein a viscosity of the non-conductive fluid is indirectly proportional to a temperature of the compressible membrane.

10. The end-effector assembly according to claim 1, wherein at least one of the first or second compressible membranes includes a compressible material embedded with a plurality of conductive particles and the distance between the conductive particles is responsive to the compression bias.

11. The end-effector assembly according to claim 10, wherein the resistance of the compressible material is responsive to the distance between the conductive particles.

12. The end-effector assembly according to claim 10, wherein the capacitance of the compressible material is responsive to the distance between the conductive particles.

* * * * *